(12) United States Patent
Griesmer et al.

(10) Patent No.: US 7,414,246 B2
(45) Date of Patent: Aug. 19, 2008

(54) ACHIEVING ACCURATE TIME-OF-FLIGHT CALIBRATIONS WITH A STATIONARY COINCIDENCE POINT SOURCE

(75) Inventors: Jerome J. Griesmer, Mentor, OH (US); Thomas L. Laurence, North Royalton, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 267 days.

(21) Appl. No.: 11/426,042

(22) Filed: Jun. 23, 2006

(65) Prior Publication Data

US 2007/0152162 A1 Jul. 5, 2007

Related U.S. Application Data

(60) Provisional application No. 60/755,919, filed on Jan. 3, 2006.

(51) Int. Cl.
*G01T 1/164* (2006.01)

(52) U.S. Cl. .............................. 250/363.09; 250/363.03; 250/370.09; 378/62

(58) Field of Classification Search ............ 250/370.09, 250/363.09, 363.03; 378/62
See application file for complete search history.

(56) References Cited

U.S. PATENT DOCUMENTS

| | | | |
|---|---|---|---|
| 5,272,343 A | 12/1993 | Stearns | |
| 5,272,344 A | 12/1993 | Williams | |
| 5,821,541 A * | 10/1998 | Tumer | 250/370.09 |
| 6,140,650 A | 10/2000 | Berlad | |
| 7,057,178 B1 | 6/2006 | Manjeshwar et al. | |
| 2003/0128801 A1* | 7/2003 | Eisenberg et al. | 378/19 |
| 2004/0065838 A1* | 4/2004 | Tumer | 250/370.09 |
| 2005/0156112 A1 | 7/2005 | Williams et al. | |
| 2006/0097175 A1 | 5/2006 | Ganin et al. | |
| 2006/0102845 A1 | 5/2006 | Williams et al. | |
| 2006/0138315 A1 | 6/2006 | Williams et al. | |
| 2006/0145082 A1 | 7/2006 | Stearns et al. | |
| 2006/0163485 A1 | 7/2006 | Stearns et al. | |

OTHER PUBLICATIONS

Thompson, C.J., et al.; A Central Positron Source to Perform the Timing Alignment of Detectors in a Pet Scanner; 2004; IEEE Record of Nuclear Science Symposium; vol. 4; pp. 2361-2365.

* cited by examiner

*Primary Examiner*—Constantine Hannaher
*Assistant Examiner*—Djura Malevic

(57) ABSTRACT

A method for calibrating an imaging system includes coincident detecting scatter radiation events from a calibration source located within a bore of the imaging system. The scatter radiation events are subsequently used to compute calibration time offsets for each detector channel in the imaging system. Each detector channel is then calibrated with respective calibration time adjustments.

26 Claims, 5 Drawing Sheets

ACHIEVING ACCURATE TIME-OF-FLIGHT CALIBRATIONS WITH A STATIONARY COINCIDENCE POINT SOURCE

CROSS REFERENCE TO RELATED APPLICATIONS

This application claims the benefit of U.S. provisional application Ser. No. 60/755,919 filed Jan. 3, 2006, which is incorporated herein by reference.

BACKGROUND

The following relates to medical imaging systems. It finds particular application to calibrating such systems. More particularly, it is directed towards calibrating the coincidence timing utilized in time-of-flight (TOF) measurements, such as those associated with Positron Emission Tomography (PET).

A conventional PET scanner has a plurality of radiation detector modules. The modules are arranged to facilitate positioning a subject such that the modules surround the subject. A radiopharmaceutical is administered to and/or ingested by the subject. The radiopharmaceutical produces radiation decay events in the subject that emit positrons. The positrons travel a relatively short distance before interacting with an electron in an electron-positron annihilation event that produces two oppositely directed gamma rays. The two oppositely directed gamma rays are detected by two different radiation detector modules as two substantially simultaneous radiation detection events that define a line of response (LOR) therebetween.

Each radiation detector module includes circuitry that facilitates determining a spatial location at which each event is received and an energy of each event, as well as other information. For example, each radiation detector module often includes one or more scintillators that produce a proportional burst or scintillation of light responsive to each gamma ray detection. However, there are time variations amongst scintillation crystals as to how quickly the radiation is converted into light, which introduces various time delays into the light signals. Further time delays are introduced due to the conversion of the light into electrical signals. Such time delays typically vary from conversion device to conversion device. With conventional PET scanners, photomultiplier tubes are commonly used to convert the light into electrical signals. The time delays associated with each tube can vary greatly from tube to tube. Additional time delays are introduced as the signals propagate through the amplifiers, reactive circuit components, along the wires, etc. to the point at which each event is digitally time-stamped. Conventionally, each channel is calibrated to compensate for these delays through time delay circuitry.

Technological advances in the medical imaging arts have led to PET scanners with a temporal resolution of about twenty-five picoseconds today and better resolution is expected in the future. With this resolution, time-delay circuits need to be accurately calibrated. Conventional time-delay calibration techniques tend to be complicated and use a large number of data channels, typically tens of thousands of channels. For example, with one technique, time-of-flight scanners are temporally calibrated by rotating a line source around a circular path and measuring the relative detection times for the 180 degrees coincident gamma rays. This calibration procedure typically includes expensive and complex equipment. In addition, if a stationary source is used, it typically is difficult to determine whether the detector at one end of the line of response is slow or the detector at the other end is fast, and the like. Further, processing techniques that minimize time differences tend to find local minimum rather than the absolute minimum, reducing calibration accuracy.

Thus, there is a need for improved calibration techniques that facilitate overcoming these deficiencies.

BRIEF SUMMARY

In one aspect, a method for calibrating an imaging system is illustrated. The method includes coincident detecting scatter radiation events from a calibration source located within a bore of the imaging system. The scatter radiation events are subsequently used to compute calibration time offsets for each detector channel in the imaging system. Each detector channel is then calibrated with respective calibration time adjustments.

One advantage includes accurately calibrating detector delay times for a TOF-PET scanner with a stationary source.

Another advantage lies in using scatter radiation to calibrate detector delay times for a TOF-PET scanner.

Another advantage resides in using a combination of scatter and 180 degree opposite coincident radiation to provide a refined calibration for a TOF-PET scanner.

Still further advantages will become apparent to those of ordinary skill in the art upon reading and understanding the detailed description of the preferred embodiments.

BRIEF DESCRIPTION OF THE DRAWINGS

The drawings are only for purposes of illustrating embodiments and are not to be construed as limiting the claims.

DETAILED DESCRIPTION OF THE PREFERRED EMBODIMENTS

Figure 1:
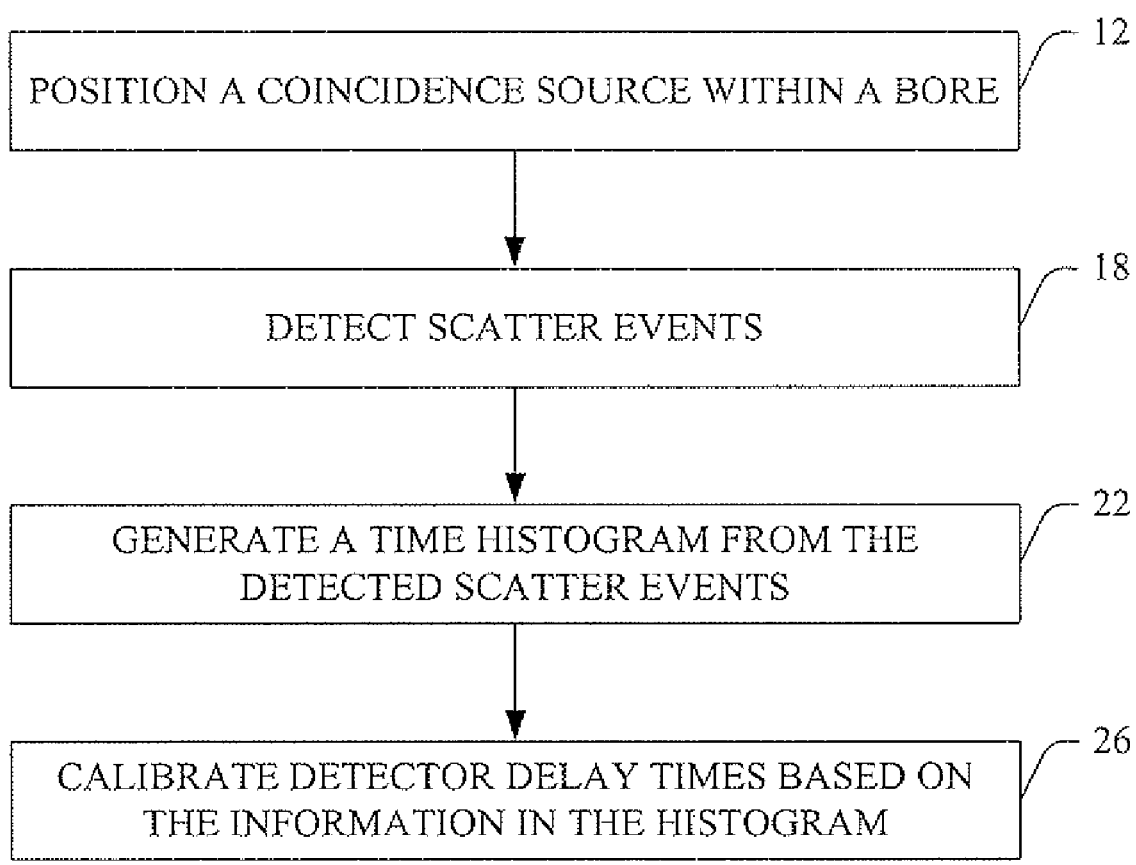
FIG. 1 illustrates a method for calibrating the coincidence timing for a PET scanner.
Figure 2:
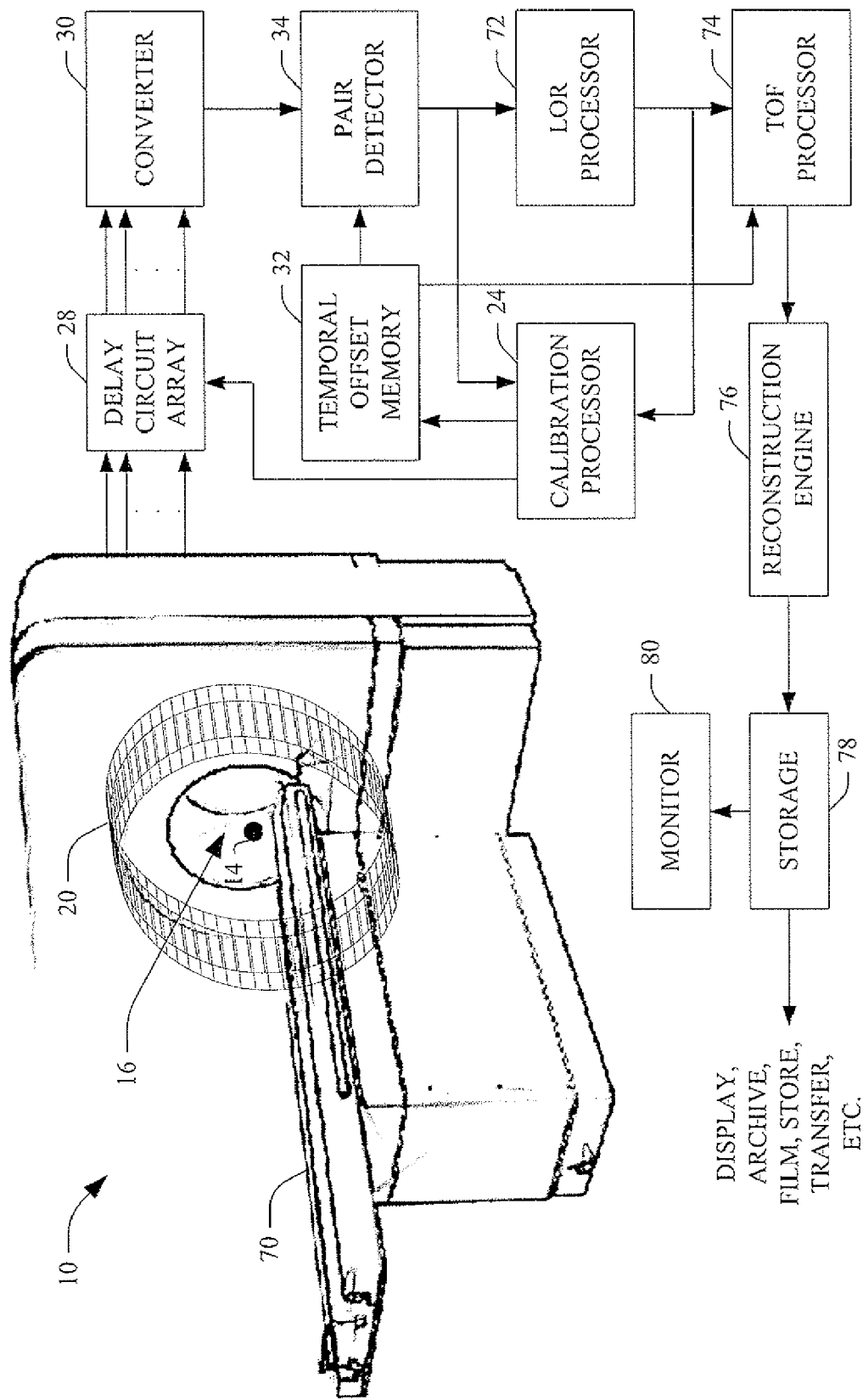
FIG. 2 illustrates an exemplary imaging system.

FIG. 1 illustrates a method for calibrating an imaging system 10 such as illustrated in FIG. 2. The calibration technique calibrates the coincidence timing utilized in time-of-flight (TOF) measurements such as those associated with Positron Emission Tomography (PET).

At reference numeral 12, a coincidence source 14 is placed within an imaging region 16 (or bore) of a PET scanner 10. The coincidence source can be a point source such as a scatter cylinder (e.g., plastic, steel, etc.), a scatter button (e.g., a 2.5 cm diameter plastic volume of Na-22), etc., or a line source. The coincidence source can be fixed at a position or mobile relative to the bore. In one instance, the coincidence source is fixed at about a center location of the bore. In another instance, the coincidence source is fixed at a known offset from the center of the bore. At 18, coincidence scatter radiation events are detected by detectors of a detector array 20. Such events are coincident events that are not 180 degrees opposite from each other across the bore. Such events arise out of electron-positron annihilation event in which one or both gamma rays are scattered and detected at substantially the same time (e.g., within a time window). Coincident events that are 180 degrees opposite from each other (non-scatter events) can be filtered. For example, an inverse region of interest (ROI) filter or other filter can be used to filter the non-scatter events.

At 22, a calibration processor 24 generates a histogram of the relative detection times of each crystal relative to a plurality of the other detectors. The 180 degrees opposite detectors are assumed to receive direct rather than scattered radiation. The travel time of the scatter events, which travel at the speed of light across the known distance to the detectors from the source to each detector is known; if the source is at about the center of the bore, the travel times are substantially equal and, if the source is offset from the center of the bore, the travel times are shifted by a known amount by the offset. This information is used to interpret the time histogram. At 26, the delay times of the detectors are calibrated based on the histogram (e.g., the centroids) to achieve substantial coincidence and applied to the corresponding on of delay circuits 28 of each to the plurality of detection channels. As needed by the specific hardware implementation, the individual detectors can be "grouped" into various subsets, such as groups near the center of each PMT tube, groups all signaling the same hardware trigger channel, etc.

The tube delay circuits 28 temporally shift analog detection signals prior to the signals being amplitude digitized and time stamped by a converter 30. Alternatively, the delay times for each detector channel can be stored in a temporal offset memory 32. A pair detector 34 or a preliminary time adjusting circuit or processor adjusts the detection time of each event in accordance with the delay times or temporal offset determined by the calibration processor 24 for the detection channel that detected it. Alternatively, delay or temporal offsets can be distributed along the scanner detector and processing systems or can be applied at other points such as during the time stamping of each event. By knowing the relative detection times of each detector relative to most of the other detectors, the calibration time delays or temporal offsets can be achieved using essentially any difference minimization techniques. Examples of suitable minimization techniques include least squares, weighted least squares, regressions, as well as other mathematical optimization techniques.

With reference again to FIG. 2, the medical imaging system 10 includes the ring of radiation detectors 20 (e.g., hundreds, thousands, etc.) arranged around the imaging region 16 to detect radiation events (e.g., gamma rays) emitted from within the imaging region 16. As depicted, the plurality of radiation detectors 44 can be arranged in multiple rings (e.g., two, ten, a hundred, etc.) of detectors along an axial direction. The scanner 10 further includes a support mechanism 70 for positioning a patient or an imaging subject in the imaging region 16. In some instances, the support mechanism 70 is linearly movable in an axial direction generally transverse to the radiation detectors 20 to facilitate acquiring three dimensional imaging data.

In preparation for imaging with the scanner 10, a suitable radiopharmaceutical is administered to the subject that will be scanned, and the subject is positioned within the imaging region 16. The radiopharmaceutical undergoes radioactive decay, which results in an emission of positrons. Each positron interacts with one or more nearby electrons and annihilates, which produces two oppositely directed (180 degree) gamma rays having energies of about 511 keV each. The two oppositely directed gamma rays may strike opposing detectors at substantially the same time, i.e., coincidentally when positions originate equidistant from the pair of detectors. There is a slight time offset between coincident events due to the different travel distances.

A typical detector head includes one or more scintillation crystals. Each scintillation crystal produces a scintillation of light when struck by a radiation event such as a gamma ray produced from positron annihilation. The light produced by each crystal is received by one or more photodetectors (not shown), typically photomultiplier tubes. Each of the photodetectors converts the light into a representative electrical signal. Each detector may also be associated with local and/or remote processing circuitry (not shown) that provides signal amplification, filtering, conditioning, etc. As described above, the conversion from gamma photon to light photons and light (photons) to electrical signal, as well as any other processing, can introduce different time delays into each of the resulting signals. The calibration techniques described above are used to adjust the delay circuits 28 or temporal offset memory 32 to compensate for these time delays.

The electrical signals are conveyed to the converter 30, which digitizes and time stamps the signals. The pair detector 34 identifies pairs of substantially simultaneous or coincident gamma ray detections belonging to corresponding electron-positron annihilation events. This processing can include, for example, energy windowing (e.g., discarding radiation detection events outside of a selected energy window disposed about 511 keV) and coincidence-detecting circuitry (e.g., discarding radiation detection event pairs temporally separated from each other by greater than a selected time-window).

Upon identifying an event pair, a line of response (LOR) processor 72 processes the spatial information for each pair of events to identify a spatial LOR connecting the two gamma ray detections. Since the two gamma rays emitted by a positron-electron annihilation event are oppositely spatially directed, the electron-positron annihilation event is known to have occurred somewhere on the LOR. In TOF-PET, the radiation detectors 20 and the time stamping of the converter 30 have sufficiently high temporal resolution to detect a time-of-flight (TOF) difference between the two substantially simultaneous gamma ray detections. A TOF processor 74 analyzes the time difference between the times of each event of the coincident pair to localize the positron-electron annihilation event along the LOR. Optionally, the temporal offset from the temporal offset memory 32 can be applied at this stage.

The result, accumulated for a large number of positron-electron annihilation events, includes a set of histoprojections. The histoprojections are conveyed to a reconstruction engine 76 that reconstructs the histoprojections to generate one or more images using a suitable reconstruction algorithm such as filtered backprojection, iterative backprojection with correction, etc.

The raw data and/or reconstructed images are stored in storage 78, and can be displayed, printed, archived, filmed, processed, transferred to another device, displayed on a monitor 80, etc. A radiologist or other suitable clinician can use the raw data and/or reconstructed image to control the TOF-PET scanner 10, diagnose the subject, etc.

It is to be appreciated that the processing described above as well as other processing can be performed by one or more processing components. Thus, the processing described herein can be processed by a single processing component, individual processing components, different combinations of processing components, and/or a combination thereof.

Figure 3:
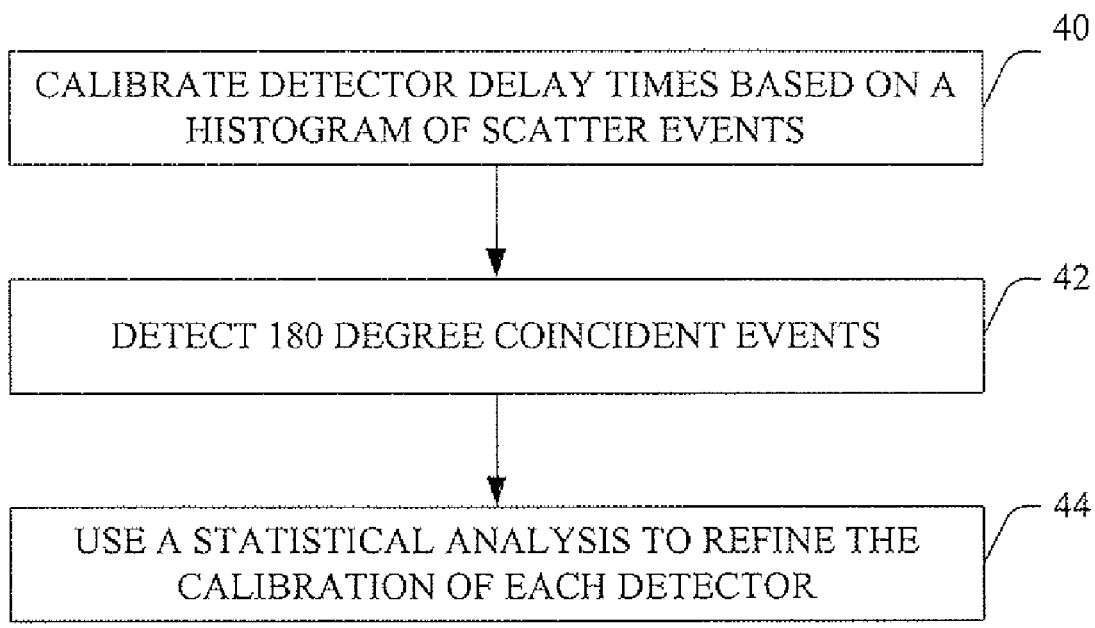
FIG. 3 illustrates a method for calibrating and subsequently refining the coincidence timing for a PET scanner.

FIG. 3 illustrates a method for calibrating and subsequently refining the coincidence timing utilized in TOF measurements. At 40, delay times for the detectors of an imaging, such as a PET, scanner are first calibrated from scatter events as described in connection with FIG. 1. For instance, a coincidence source is placed (e.g., at a fixed location) within the bore (e.g., at the center or at a known offset from the center) and scatter radiation events are detected. The unscattered histograms can be used to measure the actual source position. A histogram of the relative detection times of each crystal is generated and the centroids are used to calibrate the delay times of each detector channel.

At 42, direct (or non-scatter) coincident events that are 180 degrees opposite from each other are detected. Such events may not necessarily be exactly 180 degrees opposite. For example, a range or window (e.g., with a one, two, etc. degree tolerance) may be defined in which coincident events that fall within the window are deemed direct coincident events. If the scanner 10 functions in a list mode, the direct coincident events can be collected concurrently with the scattered events and saved for this refined calibration technique. Similar to the detected scatter events, if the source is at about the center of the bore, the travel times of the pair of events are about equal and, if the source is offset from the center of the bore, the travel times are shifted by about the offset. At 44, the calibrated delay times are fine-tuned based on the detected direct opposite coincident events. This can be achieved through various statistical deviation minimization techniques. Such minimization techniques tend to find a local minimum that may not be a global minimum. By first using the scatter radiation technique described in FIG. 1, the detectors are brought sufficiently close to the global minimum that minimizing the temporal deviations based on the direct coincident event data can achieve the global minimization of the temporal offsets.

Figure 4:
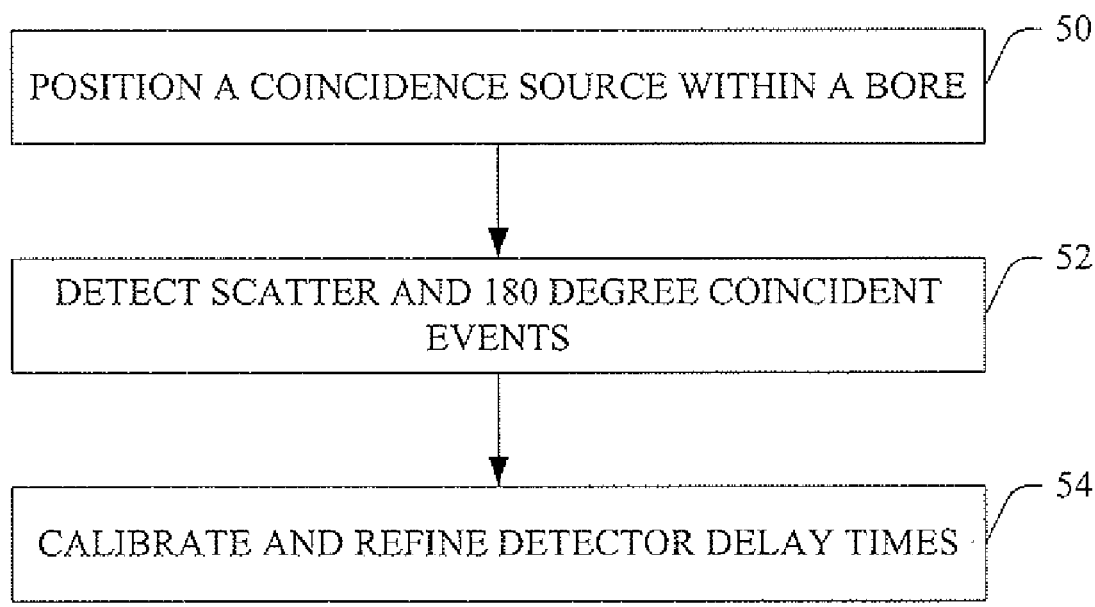
FIG. 4 illustrates a method for concurrently calibrating and refining the coincidence timing for a PET scanner.

FIG. 4 illustrates a method for concurrently calibrating and refining the coincidence timing utilized in TOF measurements. At 50, a coincidence source is placed within the bore of a PET scanner as described above. At 52, both scatter and directed coincident events are detected. These events can be serially and/or concurrently detected. By way of example, using a list mode data collection technique, a single data set with both scatter and direct coincident events is concurrently collected. This same data set can also be used for energy and/or count calibrations. At 54, the scatter and direct coincident events are used in combination to perform the initial and refined calibrations from a single acquisition rather than two back-to-back acquisitions. As described above, this includes generating a histogram from the scatter events or the direct and scatter events, calibrating the detector delay times based on the histogram and using statistical techniques, and refining the calibration with the direct or scatter coincident event data using statistical techniques.

Although the methods above are described through a series of acts, it is to be understood that in various instances, the illustrated acts can occur in a different order. In addition, in some instance, the one or more of the acts can concurrently occur with one or more other acts. Moreover, in some instance more or less acts can be employed.

Figure 5:
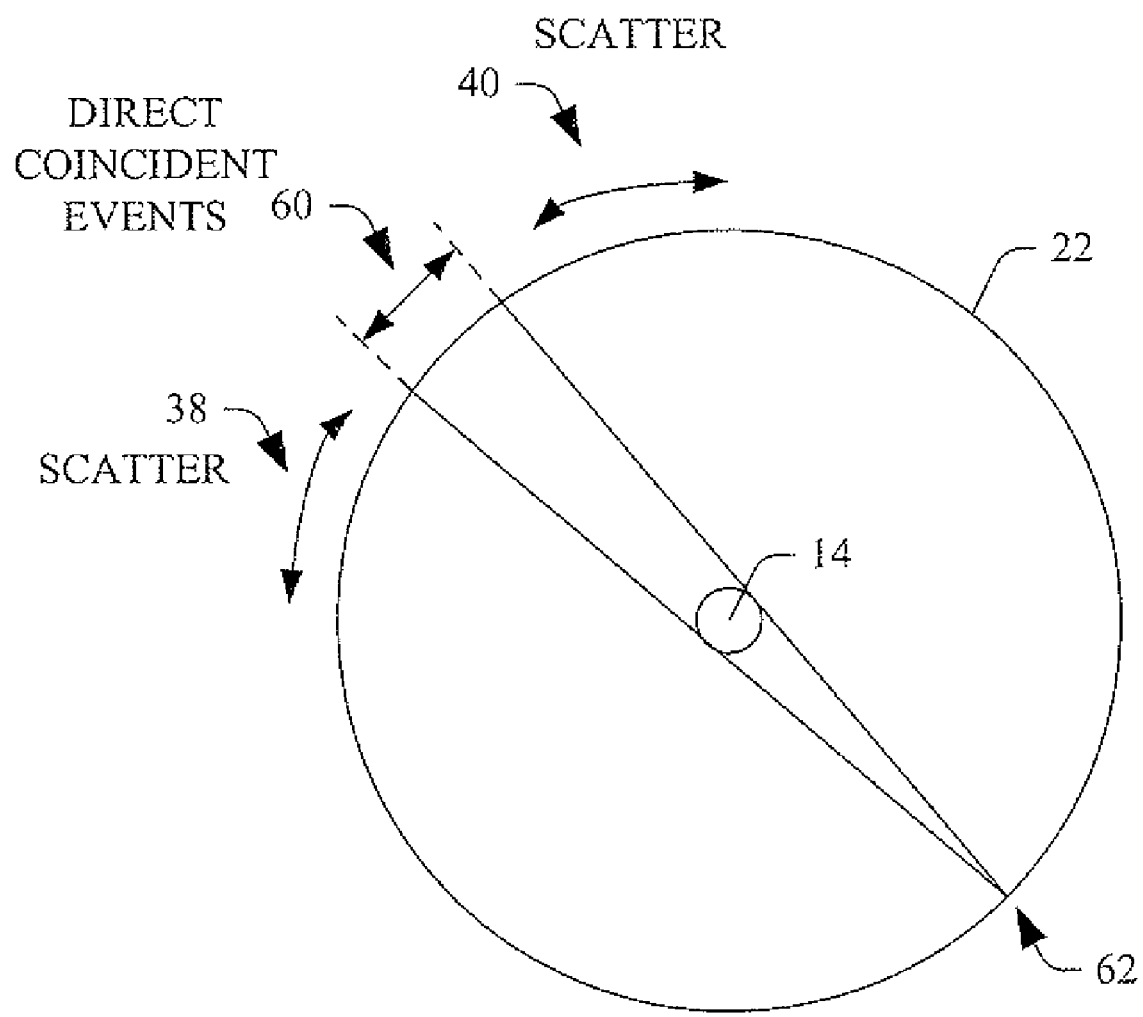
FIG. 5 illustrates a graphical representation of the calibration setup.

FIG. 5 illustrates a graphical representation showing the coincidence source 14 within a bore detector ring 20 of an imaging system and exemplary sets of detectors that are used to detect the scatter and the direct coincident events. For explanatory purpose, a point source is depicted. However, as discussed above, a line source can also be used. In addition, the point source 14 in this example is fixed at about the center of the detector ring 20, although it could be fixed at a known offset from the center. A region 60 illustrates detectors that primarily detect the direct coincident events coincident with a detector 62. The direct coincident detection region for the detector 62 is defined by the "shadow" that the source 14 casts on the ring 22, i.e., the arc segment in which straight lines that originate at detector 62 and intersect the source 14 can fall. Regions 64 and 66 illustrate detectors that primarily detect scatter events coincident with the detector 62. Events detected in the regions 64 and 66 are used to build the histogram generated in step 22.

Figure 6:
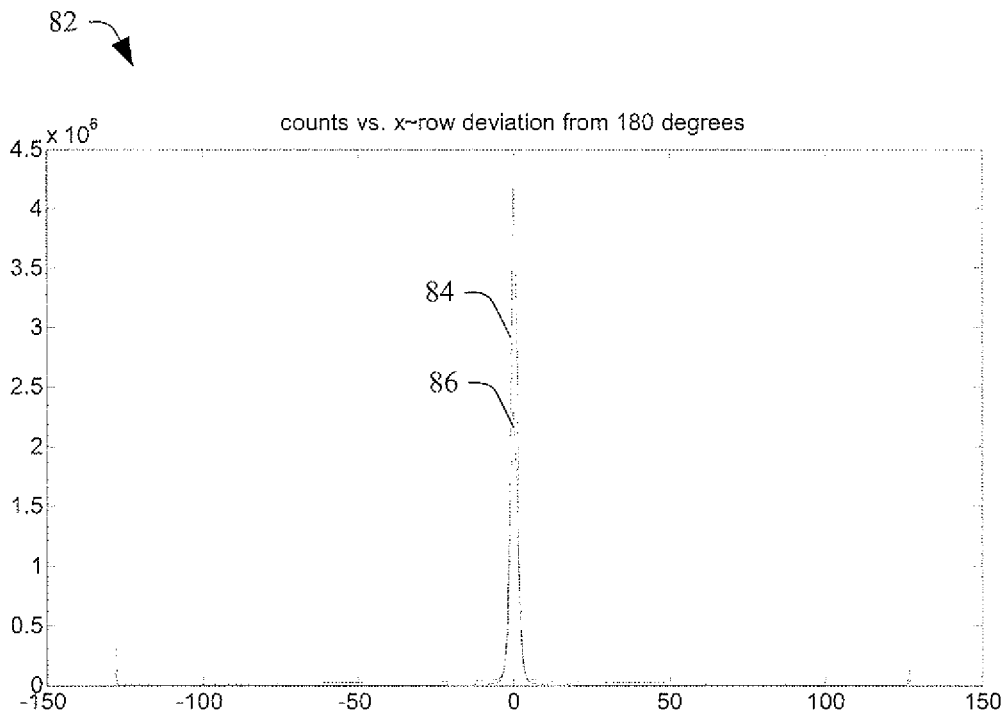
FIG. 6 illustrates a histogram showing counts versus row deviation for 180 degrees.
Figure 7:
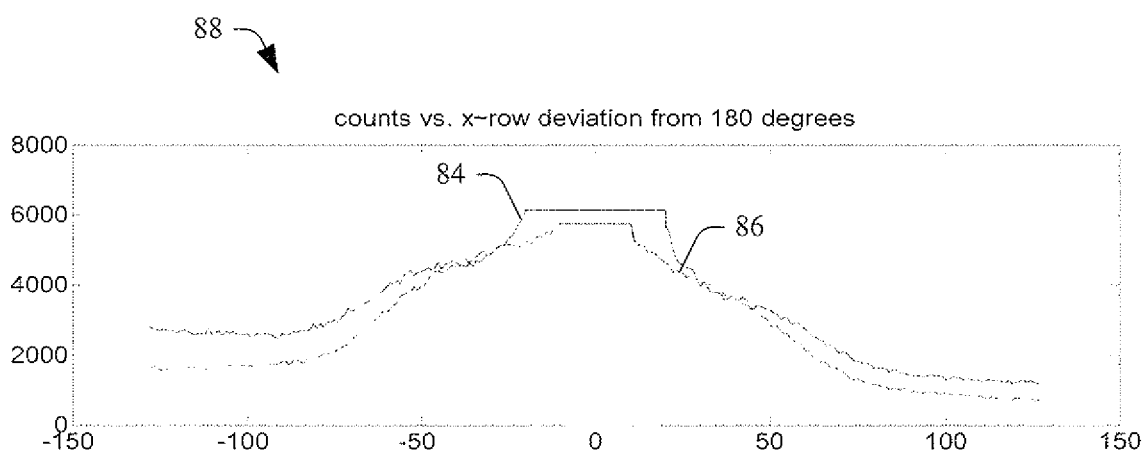
FIG. 7 illustrates a statistically leveled histogram showing counts versus row deviation for 180 degrees.

FIG. 6 illustrates a typical histogram 82 showing counts versus row deviation for 180 degrees for a Na-22 button (at 84) and a button inside of a steel scatter cylinder (at 86). For a stationary coincidence point source, the unscattered events (due to their dominant high probability) cause the resulting time histograms to reflect only a small region of the opposing detector surface for both the Na-22 button and the button inside of the steel scatter cylinder. FIG. 7 illustrates a statistically leveled histogram 88. This histogram can be generated by measuring and then using statistical weighting per degrees of scatter to more uniformly average the "opposing" detector region. That is, the binary ROI edge (scattered, unscattered) is statistically smoothed into a uniform larger region.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A method for calibrating an imaging system, comprising:
   coincident detecting scatter radiation events from a calibration source located within an imaging region of the imaging system;
   computing a calibration time offset for at least one detector channel in the imaging system based on the detected scatter radiation events; and
   calibrating the at least one detector channel with the calibration time offset.

2. The method as set forth in claim 1, further including:
   generating a time histogram from the detected scatter radiation events; and
   using the histogram to compute the calibration time offset for the at least one detector.

3. The method as set forth in claim 2, wherein the time histogram is statistical weighted per degrees of scatter to more uniformly average the detector region.

4. The method as set forth in claim 1, wherein computing the calibration time offset includes applying a difference minimization technique.

5. The method as set forth in claim 1, wherein the calibration time offset is computed by determining a global minimum.

6. The method as set forth in claim 1, further including:
   fixing the position of the calibration source with respect to the bore to a stationary position during the detecting step.

7. The method as set forth in claim 1, further including:
   positioning the calibration source at one of a geometric center of the bore and at a predefined offset from the center of the bore.

8. The method as set forth in claim 1, further including:
   detecting coincident direct radiation events, and wherein the computing step includes:
   initially calibrating the time offset for the at least one detector channel using the scatter detected scatter radiation events; and refining the time offset with the detected direct radiation events.

9. The method as set forth in claim 8, further including:
concurrently detecting the scatter events and the direct coincident events using a list mode data collection technique.

10. The method as set forth in claim 8, further including:
using a combination of the scatter and the direct coincident events to determine and refine the calibration time offset in a single process.

11. The method as set forth in claim 8, further including:
generating a time histogram from the coincidentally detected scatter radiation events;
using the histogram to initially compute the calibration time offset for the at least one detector; and
refining the time offset via a statistical technique.

12. The method as set forth in claim 11, wherein the time histogram is statistical smoothed to form a more uniform detector region.

13. A method for calibrating a time-of-flight imaging system, comprising:
positioning a calibration source at a fixed, stationary position within an imaging region of the imaging system;
coincidence detecting scatter events emitted from the calibration source at the fixed, stationary position;
generating a time histogram from the detected scatter events; and
calibrating a time delay for a channel based on the time histogram.

14. The method as set forth in claim 13, further including:
determining a line of response between coincident direct radiation events;
localizing positron-electron annihilation events along the line of response in accordance with the corrected detection times to generate histoprojections; and
reconstructing the histoprojections to generate an image.

15. A computer medium programmed to cause a computer to import coincident detection scatter radiation event data; compute one or more calibration time offsets for one or more detector channels based on the scatter radiation events data; and calibrate the one or more detector channels with respective calibration time adjustments.

16. An apparatus for calibrating an imaging system, comprising:
a means for coincident detecting scatter radiation events from a calibration source located within an imaging region of the imaging system;
a means for computing calibration time adjustments for a plurality of detector channels in the imaging system based on the detected scatter radiation events; and
a means for calibrating at least one of the plurality of detector channels with respective calibration time adjustments.

17. The apparatus as set forth in claim 16, wherein the calibration source is one of a point and a line source.

18. A time-of-flight imaging apparatus, comprising:
a plurality of radiation detectors that generate analog signals indicative of each detected radiation event on a plurality of detector channels;
a converter that digitizes the analog signals into digitized energy and time stamp signals;
a coincidence detector that determines coincident pairs of scattered radiation events and direct radiation events; and
a calibration processor that computes a time adjustment for at least one of the plurality of radiation detectors using at least the scattered radiation event pairs.

19. The imaging apparatus as set forth in claim 18, wherein the calibration processor generates a time histogram from the detected scatter radiation events and uses the time histogram to compute the calibration time adjustment.

20. The imaging apparatus as set forth in claim 18, wherein the calibration processor uses a combination of the scatter and the direct coincident events to determine and refine the calibration time adjustment in a single process.

21. The imaging apparatus as set forth in claim 18, further comprising:
a means for correcting detection times for at least the coincident radiation events in accordance with the computed time adjustments;
a time of response processor that determines a line of response between coincident direct radiation events;
a time of flight processor that localizes a positron-electron annihilation event along the line of response in accordance with the corrected detection times to generate histoprojections; and
a reconstruction processor that reconstructs the histoprojections to generate an image.

22. A method, comprising:
computing a calibration time offset for at least one detector channel in an imaging system based on detected scatter radiation events; and
calibrating a time offset of the at least one detector channel of the imaging system based on the calibration time offset.

23. The method as set forth in claim 22, further including:
calibrating the calibrated time offset of the at least one detector channel based on detected direct radiation events.

24. The method as set forth in claim 22, further including:
calibrating the time offset of the at least one detector channel of the imaging system based on a combination of the detected scatter radiation events and detected direct radiation events in a single step.

25. A method, comprising:
generating a time histogram for coincidence detected scatter events emitted from a calibration source in an imaging region of the imaging system; and
calibrating a time delay for a detector channel of the imaging system based on the time histogram.

26. The method of claim 25, further comprising: calibrating time delay by statistically smoothing the time histogram.

* * * * *